(12) United States Patent
Misner et al.

(10) Patent No.: US 8,529,919 B2
(45) Date of Patent: Sep. 10, 2013

(54) PERSONAL CARE PRODUCT AND MANUFACTURE THEREOF

(75) Inventors: Steve Misner, Verona, NJ (US); Richard Adams, Monmouth Junction, NJ (US); Richard Blume, Budd Lake, NJ (US); Nilsa Rodriguez, Perth Amboy, NJ (US); Ronald Edward Growe, Jr., Flanders, NJ (US)

(73) Assignee: Colgate-Palmolive Company, New York, NY (US)

( * ) Notice: Subject to any disclaimer, the term of this patent is extended or adjusted under 35 U.S.C. 154(b) by 166 days.

(21) Appl. No.: 12/863,646

(22) PCT Filed: Jul. 6, 2010

(86) PCT No.: PCT/US2010/041009
§ 371 (c)(1),
(2), (4) Date: Jul. 20, 2010

(87) PCT Pub. No.: WO2012/005720
PCT Pub. Date: Jan. 12, 2012

(65) Prior Publication Data
US 2012/0009135 A1 Jan. 12, 2012

(51) Int. Cl.
*A61K 8/02* (2006.01)
*A61Q 15/00* (2006.01)
*A45D 40/16* (2006.01)
*B43K 27/00* (2006.01)

(52) U.S. Cl.
USPC ................................ 424/401; 424/65; 424/63

(58) Field of Classification Search
None
See application file for complete search history.

(56) References Cited

U.S. PATENT DOCUMENTS

| | | |
|---|---|---|
| 3,279,999 A | 10/1966 | Harrison et al. |
| 3,479,429 A | 11/1969 | Morshauser et al. |
| 4,786,449 A | 11/1988 | Smit |
| 4,937,069 A | 6/1990 | Shin |
| 5,069,897 A | 12/1991 | Orr |
| 5,102,656 A | 4/1992 | Kasat |

(Continued)

FOREIGN PATENT DOCUMENTS

| | | |
|---|---|---|
| JP | 2007 261950 | 10/2007 |
| KR | 100810798 | 3/2008 |
| WO | WO 00/67712 | 11/2000 |
| WO | WO 2005/025523 | 3/2005 |

OTHER PUBLICATIONS

International Search Report and Written Opinion for International Application No. PCT/US2010/041009 mailed Mar. 23, 2011.

(Continued)

*Primary Examiner* — Rachael E Bredefeld
(74) *Attorney, Agent, or Firm* — Michael F. Morgan

(57) ABSTRACT

Disclosed is a package for a personal care composition, the package comprising a container containing a personal care composition, the container having a base comprising a base face for standing the package on a planar surface, and a cap removably connected to and covering a dispensing end of the container opposite to the base. The cap has an end face which is inclined to the base face, and the container and cap are shaped to permit the package, independent of the amount of the personal care composition contained within the container, selectively to be stood on the base face in an upright orientation on the planar surface or on the end face in an inverted orientation on the planar surface.

21 Claims, 3 Drawing Sheets

(56) References Cited

U.S. PATENT DOCUMENTS

| | | | |
|---|---|---|---|
| 6,007,799 A | 12/1999 | Lee et al. | |
| D443,951 S | 6/2001 | Look | |
| D444,265 S | 6/2001 | Look | |
| D444,593 S | 7/2001 | Look | |
| D444,913 S | 7/2001 | Look | |
| D449,405 S | 10/2001 | Gersten et al. | |
| D450,882 S | 11/2001 | Colwell | |
| D452,585 S | 12/2001 | Look | |
| D452,587 S | 12/2001 | Look | |
| 6,338,840 B1 | 1/2002 | Allan et al. | |
| D456,560 S | 4/2002 | Gersten et al. | |
| 6,375,937 B1 | 4/2002 | Chopra et al. | |
| 6,375,938 B1 * | 4/2002 | Clothier, Jr. et al. | 424/65 |
| D456,941 S | 5/2002 | Gersten et al. | |
| D457,263 S | 5/2002 | Gersten et al. | |
| D457,264 S | 5/2002 | Gersten et al. | |
| 6,495,097 B1 | 12/2002 | Streit et al. | |
| 6,503,491 B2 | 1/2003 | Guenin et al. | |
| 6,506,369 B2 | 1/2003 | Ambler et al. | |
| 6,569,438 B1 | 5/2003 | Banowski et al. | |
| 6,610,648 B2 | 8/2003 | McGee et al. | |
| 6,723,269 B2 | 4/2004 | Grosz | |
| 6,752,982 B2 | 6/2004 | Colwell et al. | |
| 6,776,981 B2 | 8/2004 | Elliott et al. | |
| 6,838,032 B2 | 1/2005 | Grosz et al. | |
| 6,936,242 B2 | 8/2005 | Elliott et al. | |
| 6,960,338 B2 | 11/2005 | Li et al. | |
| 7,073,965 B2 | 7/2006 | Look et al. | |
| 7,074,394 B2 | 7/2006 | Li et al. | |
| 7,105,691 B2 | 9/2006 | Holerca et al. | |
| 2002/0155077 A1 | 10/2002 | Galante et al. | |
| 2003/0111130 A1 * | 6/2003 | Dugdale et al. | 141/9 |
| 2004/0047822 A1 | 3/2004 | Zamudo-Tena et al. | |
| 2004/0109833 A1 | 6/2004 | Tang et al. | |
| 2004/0198998 A1 | 10/2004 | Holerca et al. | |
| 2005/0100570 A1 | 5/2005 | Wei et al. | |
| 2005/0191254 A1 | 9/2005 | Walling et al. | |
| 2006/0204463 A1 | 9/2006 | Tang et al. | |
| 2007/0167338 A1 | 7/2007 | McHugh et al. | |
| 2007/0196308 A1 | 8/2007 | Popoff et al. | |
| 2008/0187504 A1 | 8/2008 | Fan et al. | |
| 2008/0196787 A1 * | 8/2008 | Comstock et al. | 141/9 |

OTHER PUBLICATIONS

Written Opinion in International Application No. PCT/US10/00041009, mailed Sep. 27, 2012.

* cited by examiner

PERSONAL CARE PRODUCT AND MANUFACTURE THEREOF

FIELD

The present invention relates to a personal care product including a personal care composition, for example an antiperspirant composition or a deodorant composition, in the form of a solid composition, typically a stick. The present invention also relates to the manufacture of such a personal care product.

BACKGROUND

There are various techniques to provide a unique appearance to a packaged product. Many techniques are directed to the use of colored containers and attractive labeling. Another technique is to use the product to additionally provide part of the overall unique appearance of the product.

It is known to provide personal care compositions having a random or non-random patterned appearance. Some of these compositions are an antiperspirant composition and/or a deodorant composition in the form of a stick.

Nevertheless, there is a need in the art for a personal care composition, for example an antiperspirant composition and/or a deodorant composition, which has a distinctive aesthetic appearance as compared to known products.

There is also a need in the art for a package for a personal care composition, for example an antiperspirant composition and/or a deodorant composition, that has a random diffuse pattern yet can be reliably and repeatably manufactured in large commercial volumes.

There is furthermore a need in the art for a product comprising an antiperspirant composition and/or a deodorant composition, which is in stick form and exhibits improved aesthetic appeal.

BRIEF SUMMARY

An aim of this invention is to provide a package for a personal care composition, for example an antiperspirant composition or a deodorant composition, which can at least partially meet at least one of the needs identified above.

Another aim of this invention is to provide a method for producing such a personal care composition, for example an antiperspirant composition or a deodorant composition, which can at least partially meet at least one of the needs identified above.

The present invention accordingly provides personal care product, the product comprising a container containing a solid body of a topical personal care composition, the personal care composition having at least two components having differing visual characteristics, the components being mixed to form a random diffuse pattern, first and second components of the at least two components comprising major and minor proportions by volume of the solid body, the first component having a lower melting temperature than the melting temperature of the second component.

The melting temperature of the first component may optionally be at least 23° C. lower than the melting temperature of the second component, for example 23 to 28° C. lower than the melting temperature of the second component.

Typically, the personal care composition is an antiperspirant composition and/or a deodorant composition.

The personal care composition may be a solid stick or soft solid.

The personal care composition may comprise an antiperspirant active that is present in an amount of 5 to 25% by weight of the composition.

Optionally, each of the at least two components of the personal care composition comprises the antiperspirant active.

The personal care composition may comprise a deodorant active that is present in an amount of greater than 0 to up to 1% by weight of the composition.

Optionally, each of the at least two components of the personal care composition comprises the deodorant active.

The first and second components may respectively include different first and second gellant compositions to provide different respective melting temperatures of the first and second components of the personal care composition.

Optionally, the first gellant composition comprises at least one soybean oil having an iodine value of greater than 0 to 20 and at least one fatty alcohol and the second gellant composition comprises at least one soybean oil having an iodine value of greater than 0 to 20 and at least one hydrocarbon of the formula $C_nH_{2n+2}$, wherein n is 20 to 100, and the hydrocarbon is at least 90% linear. Typically, the iodine value is 1 to 5.

The soybean oil may be present in an amount up to about 20% by weight of the respective component of the at least two components, typically in an amount up to 10% by weight of the respective component of the at least two components, more typically in an amount of 3 to 7% by weight of the respective component of the at least two components.

The at least one fatty alcohol may be present in the first component in an amount of 5 to 25% by weight of the first component. Typically, the fatty alcohol comprises stearyl alcohol.

The at least one hydrocarbon may be present in the second component in an amount of 5 to 25% by weight of the second component. Typically, the at least one hydrocarbon comprises polyethylene.

Optionally, the personal care composition further comprises silicone which is present in each of the at least two components in an amount of 5 to 70% by weight of the respective component. Typically, the silicone comprises cyclomethicone.

Optionally, the personal care composition further comprises an emollient chosen from PPG-14 butyl ether, C12-15 alkyl benzoate, phenyl trimethicone, PPG-3 myristyl ether, myristyl myristate, and combinations thereof.

Typically, the at least two components have different colors.

The present invention further provides a method of forming in a container a random diffuse pattern mixture of at least two components of a solid body of a topical personal care composition, the at least two components having differing visual characteristics, the method comprising the steps of:
(a) providing a container on a container support capable of rotating the container;
(b) feeding a first component of the at least two components into the container, the first component being molten and at a first temperature above a melting temperature of the first component;
(c) at least after commencement of step (b), feeding a second component of the at least two components into the container, the second component being molten and at a second temperature above a melting temperature of the second component, the second temperature being higher than the first temperature and the melting temperature of the second component being higher than the melting temperature of the first component;

(d) concurrently rotating the container on the container support in at least a first rotational direction during at least a part of feeding step (c) to form a random diffuse pattern mixture of the first and second components; and (e) cooling the first and second components to form a solid body having the random diffuse pattern mixture, the second component commencing solidification thereof during the cooling step prior to solidification of the first component.

Optionally, the melting temperature of the first component is at least 47° C., typically 47 to 53° C., lower than the melting temperature of the second component.

Optionally, the second temperature is at least 70° C., typically 70 to 76° C., higher than the first temperature.

Typically, the first temperature is 47 to 53° C. and the second temperature is 70 to 76° C. For example, the first temperature may be from 62 to 69° C. and the second temperature may be from 79 to 86° C.

Optionally, the second component terminates solidification thereof during the cooling step prior to solidification of the first component.

Optionally, the first and second components respectively include different first and second gellant compositions to provide different respective melting temperatures of the first and second components of the personal care composition.

Typically, the feeding of the second component in step (c) is commenced after termination of the feeding of the first component in step (b).

Optionally, the container is rotated on the container support additionally during at least a part of feeding step (c). Optionally, the container is rotated on the container support after the termination of both feeding step (b) and feeding step (c).

Optionally, the container is rotated on the container support additionally during at least a part of cooling step (e).

The container is typically rotated on the container support in an oscillating manner in the first rotational direction and in an opposite second rotational direction. For example, the container is rotated at least 90 degrees in a first direction and at least 90 degrees in a second direction. Typically, the container is rotated up to about 360 degrees in a first direction and up to about 360 degrees in a second direction. The container may be rotated up to about 270 degrees in the first direction and up to about 270 degrees in the second direction.

Optionally, the container support maintains the container at an angle of up to about 20 degrees to a vertical orientation.

Optionally, the container is subject to a vibration during the feeding of at least the second component to the container.

The first and second components may be fed into the container from a nozzle having two inputs and two outputs, one input and output pair for each respective component.

In one aspect, the present processes can produce random diffuse patterns of personal care composition in containers. By random diffuse pattern is meant an irregular pattern that has a discernable artistic yet non-geometric pattern, but where the pattern varies in dimensions and the color varies in color density to provide a color gradation throughout the personal care composition. In one embodiment there may be strongly differentiated regions and/or lines of different color, for example a darker color composition dispersed randomly and diffusely in lighter color matrix. The results are unique and very artistic patterns.

The solid personal care composition in the container may have a marbleized appearance or a swirl pattern. When the container is transparent or translucent, the pattern is continuously visible. When the container is opaque, the pattern is visible when the product is used, for example when a working surface of the topical personal care composition is revealed to the user, typically when the upper surface of a stick is exposed for topical application to the skin.

DETAILED DESCRIPTION

It should be understood that the detailed description and specific examples, while indicating embodiments of the invention, are intended for purposes of illustration only and are not intended to limit the scope of the invention.

The citation of references herein does not constitute an admission that those references are prior art or have any relevance to the patentability of the invention disclosed herein. Any discussion of the content of references cited in the Background is intended merely to provide a general summary of assertions made by the authors of the references, and does not constitute an admission as to the accuracy of the content of such references. Each and every reference cited herein is hereby incorporated by reference in its entirety.

The detailed description, while indicating embodiments of the invention, is intended for purposes of illustration only and is not intended to limit the scope of the invention. Moreover, recitation of multiple embodiments having stated features is not intended to exclude other embodiments having additional features, or other embodiments incorporating different combinations the stated of features.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include", and its variants, is intended to be non-limiting, such that recitation of items in a list is not to the exclusion of other like items that may also be useful in the dispensers of this invention.

The invention will now be described in more detail in its preferred embodiments with reference to the drawings. The described products and processes may be modified in minor details without departing from the concept of the present invention. As used throughout this description, ranges are used as a shorthand for describing each and every value that is within the range. Any value within the range can be selected as the terminus of the range.

Figure 1:
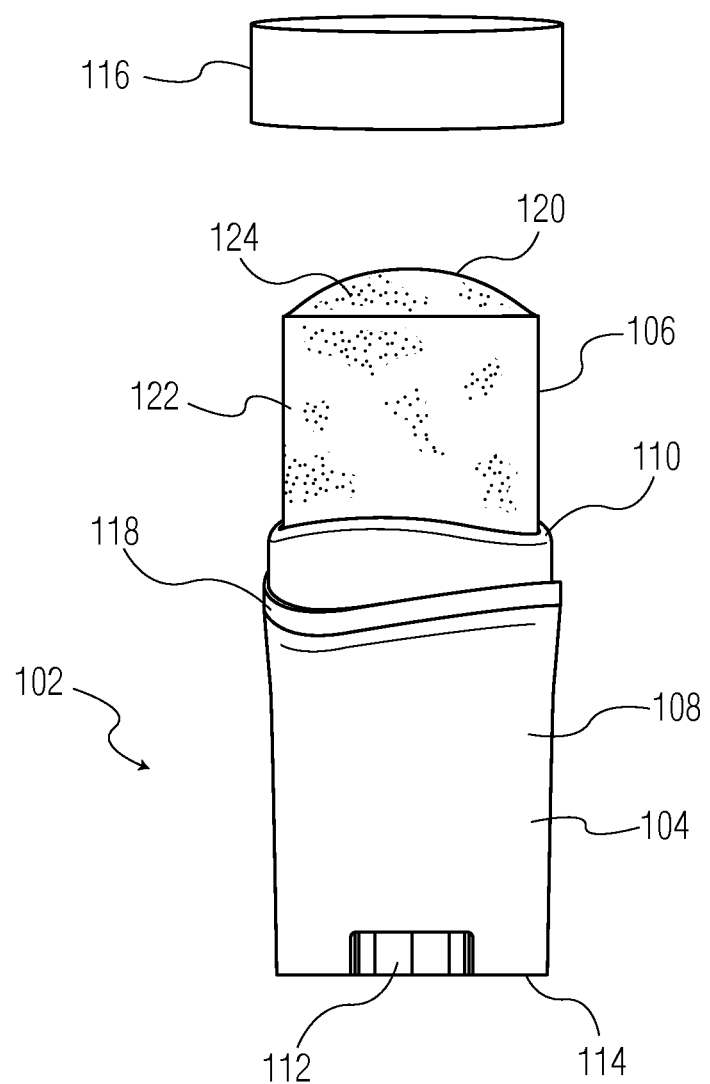
FIG. 1 schematically illustrates a front view of a personal care product including a personal care composition having a random diffuse pattern in accordance with an embodiment of the present invention.

FIG. 1 schematically illustrates a front view of a personal care product including a personal care composition having a random diffuse pattern in accordance with an embodiment of the present invention.

The personal care product, designated generally as 102, comprises a container 104 containing a solid body 106 of a topical personal care composition.

The personal care composition is an antiperspirant composition and/or a deodorant composition, and may comprise an antiperspirant active that is present in an amount of 10 to 25% by weight of the composition and/or a deodorant active which is present in an amount of greater than 0 to up to 1% by weight of the composition.

The container 104 comprises a conventional housing 108 having a cavity 110 for containing a solid body 106 formed as a hard stick or soft solid. A mechanism 112 for advancing or retracting the solid body 106 relative to the housing 108 is provided at the base 114 of the housing 108. A removable cap 116 may be fitted to the upper end 118 of the housing 108 to cover the exposed end 120 of the solid body 106. In FIG. 1, the solid body 106 has been advanced partly from out of the cavity 10 to illustrate the visual appearance of the solid body 106.

The personal care composition has at least two components 122, 124, called first and second components, having differing visual characteristics. In alternative embodiments, greater than two visually distinct components may be provided. The at least two components may each comprise the antiperspirant active and/or the deodorant active. The two components differ in color.

The first and second components 122, 124 are mixed to form a random diffuse pattern. The first and second components 122, 124 comprise major and minor proportions by volume of the solid body 106. Typically, the first component 122 comprises 70 to 95 wt %, typically 85 wt % and the second component 124 comprises 5 to 30 wt %, typically 15 wt %, of the solid body 106. Most typically, the second component 124 comprises the darker color composition dispersed randomly and diffusely in the lighter color matrix comprised of the first component 122.

The first component 122 has a lower melting temperature than the melting temperature of the second component 124. Typically, the melting temperature of the first component 122 is at least 28° C. lower than the melting temperature of the second component 124. For example, the melting temperature of the first component 122 is 47 to 53° C. lower than the melting temperature of the second component 124.

Having the components melt at different temperatures makes it easier to form striations or marbleized patterns in the composition. The higher melting point material solidifies first to start forming a solid that is mixed within the liquid lower melting point component. In certain embodiments, an inline mixer is not needed to mix the components.

In this embodiment, the different melting temperatures of the first and second components 122, 124 is achieved by providing that the first and second components 122, 124 respectively include different first and second gellant compositions. For example, the first gellant composition comprises at least one soybean oil having an iodine value of greater than 0 to 20 and at least one fatty alcohol and the second gellant composition comprises at least one soybean oil having an iodine value of greater than 0 to 20 and at least one hydrocarbon of the formula $C_nH_{2n+2}$, wherein n is 20 to 100, and the hydrocarbon is at least 90% linear.

The soybean oil in the first and second components 122, 124 may be the same soybean oil. Typically, the iodine value is 1 to 5. The soybean oil may be present in an amount up to about 20% by weight, more typically up to about 10% by weight, for example 3 to 7% by weight, of the respective component of the at least two components.

The at least one fatty alcohol may be present in the first component in an amount of 5 to 25% by weight of the first component. The fatty alcohol typically comprises stearyl alcohol.

The at least one hydrocarbon may be present in the second component in an amount of 5 to 25% by weight of the second component. The at least one hydrocarbon may comprise polyethylene.

The personal care composition typically further comprises silicone which is present in each of the at least two components in an amount of 5 to 70% by weight of the respective component. The silicone may comprise cyclomethicone.

The personal care composition may further comprise an emollient chosen from PPG-14 butyl ether, C12-15 alkyl benzoate, phenyl trimethicone, PPG-3 myristyl ether, myristyl myristate, and combinations thereof.

The composition is a solid stick or soft solid when at ambient room temperature of about 25° C. The stick form is an example of a solid form, and the soft solid is a thickened form that may or may not be solid. The stick form can be distinguished from a soft solid in that, in a stick, the formulated product can retain its shape for extended time periods outside the package, the product not losing its shape significantly (allowing for some shrinkage due to solvent evaporation). Adjustment of amounts of gelling or thickening agents can be used in order to form a soft solid or stick.

Soft solids can be suitably packaged in containers that have the appearance of a stick, but which dispense through apertures (for example, slots or pores) on the top surface of the package. The soft solid products have also been called soft sticks or "smooth-ons", and hereinafter are generically called "soft solids". Reference is made to U.S. Pat. Nos. 5,102,656, 5,069,897, and 4,937,069, each of which discloses such soft solids, including physical characteristics thereof such as viscosity and hardness. The contents of each of these three U.S. patents are incorporated herein by reference to the extent that they do not conflict with the disclosure herein.

Gelling Agents

Gelling agents used in the topical personal care compositions used in the present invention comprise hydrogenated soybean oil as a first gellant and a second gellant comprising a fatty alcohol for the first component 122 or a hydrocarbon of the formula $C_nH_{2n+2}$, wherein n is 20 to 100, and the hydrocarbon is at least 90% linear for the second component 124.

The hydrogenated soybean oil is used as a co-gellant along with the selected second gellant to provide a solid stick or soft solid antiperspirant. The hydrogenated soybean oil is almost, but not fully hydrogenated. The amount of hydrogenation is measured by the iodine value. The iodine value can be measured by ASTM D5554-95 (2006). The iodine value of the hydrogenated soybean oil used herein is greater than 0 to 20. In one embodiment, the iodine value is 1 to 5. It has been found that this level of hydrogenation provides the desired structure to the antiperspirant and provides a softer and creamier application aesthetics.

The hydrogenated soybean oil is present in an amount up to about 20% by weight of the composition. In another embodiment, the amount is up to about 10% by weight. In one embodiment, the amount is 3 to 7% by weight. In another embodiment, the amount is 4 to 6% by weight.

The hydrogenated soybean oil can provide increased fragrance longevity when used to replace hydrogenated castor oil.

The fatty alcohol can be any fatty alcohol. In one embodiment, the fatty alcohol is stearyl alcohol.

The hydrocarbon is a hydrocarbon of the formula $C_nH_{2n+2}$, wherein n is 20-100, and the hydrocarbon is at least 90% linear. In one embodiment, the hydrocarbon is a paraffin. In another embodiment, the hydrocarbon is polyethylene. An example of a polyethylene can be found in U.S. Pat. No. 6,503,491, which is incorporated herein by reference only for its disclosure of the polyethylene. In another embodiment, the polyethylene has a weight average molecular weight in of 300 to 3000 and a melting point of 50 to 129° C.

In one embodiment, the second gellant, comprising the fatty alcohol or the hydrocarbon as discussed above, is present in the composition in an amount of 5 to 25% by weight of the composition. In another embodiment, the amount is 10 to 20% by weight.

The formulations of the invention may further comprise additional gelling agents, which include, but are not limited to, waxes, esters of fatty acid and fatty alcohol, triglycerides, or other cosmetically acceptable materials, which are solid or semi solid at room temperature and provide a consistency suitable for application to the skin.

When using the hydrogenated soybean oil as a co-gellant with the fatty alcohol gellant, the composition has increased fragrance retention as compared to known compositions containing hydrogenated castor oil.

Volatile Silicone

Compositions according to the present invention may include a volatile silicone. In one embodiment, the volatile silicone is a volatile cyclic polydimethylsiloxane (cyclomethicone), e.g., cyclopentasiloxane. By volatile material it is meant that the material has a measurable vapor pressure at ambient temperature. Preferably, the volatile cyclic polydimethylsiloxane is cyclomethicone. Various types of cyclomethicones may be used. Illustratively, and not by way of limitation, the volatile silicones are one or more members selected from cyclic polydimethylsiloxanes such as those represented by Formula I:

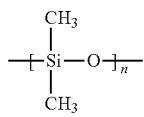

where n is an integer with a value of 3-7, particularly 5-6. Illustrative examples of suitable cyclomethicones are DC-345 and DC-245, manufactured by Dow Corning Corporation, Midland, Mich. These types include a tetramer (octylmethylcyclotetrasiloxane) and a pentamer (decamethylcyclopentasiloxane). In one embodiment, the amount of volatile silicone in the composition is 5 to 70% by weight of the composition. In another embodiment, the amount is 25 to 45% by weight.

Antiperspirant Active Materials

When the composition includes an antiperspirant active, any of the known antiperspirant active materials can be utilized in the composition. Antiperspirant actives include, but are not limited to, aluminum chlorhydrate, aluminum chloride, aluminum sesquichlorohydrate, aluminum-zirconium hydroxychlorides, complexes or adducts of the above-mentioned active ingredients with glycol, such as propylene glycol (for example, "Rehydrol" II from Reheis Chemical Co.), and combinations thereof. Known aluminum-zirconium salts in combination with neutral amino acids, such as glycine (e.g., aluminum-zirconium tetrachlorohydrex Gly) can also be used. Generally, any of the Category I active antiperspirant ingredients, listed in the Food and Drug Administration's Monograph on Antiperspirant Drug Products for overall-the-counter human use (Oct. 10, 1973) can be used.

In other embodiments, the antiperspirant active is an aluminum salt and/or an aluminum-zirconium salt, such as those described above, that are further stabilized by betaine and a calcium salt. More information about betaine and calcium salt stabilized antiperspirant salts can be found in U.S. Patent Application Publication No. 2006/0204463 to Tang et al., which is incorporated herein by reference only for the disclosure of the antiperspirant actives.

In other embodiments, the antiperspirant active, such as those described above, is selected to have a low metal to chloride ratio. Examples of these antiperspirant actives can be found in U.S. Pat. No. 6,375,937 to Chopra et al. and in U.S. Patent Application Publication No. 2004/0109833 to Tang et al., which are incorporated herein by reference only for their disclosure of the antiperspirant active.

In other embodiments, the type of salt of interest, an aluminum zirconium tetrasalt or octasalt free of glycine are used wherein aluminum zirconium salt is stabilized by Betaine and has a metal to chloride ratio of 0.9:1 to 1.3:1 (and in other embodiments of 0.9:1 to 1.2:1 or 0.9:1 to 1.1:1). For the tetrasalt, the Al/Zr atomic ratio can be 3.2:1 to 4.1:1.0 and the Betaine:zirconium mole ratio can be 0.2:1 to 3.0:1 (or in other embodiments of 0.4:1 to 1.5:1). Another salt that can be used is an aluminum chloride salt buffered by Betaine, wherein the salt has a metal to chloride ratio of 0.9:1 to 1.3:1 (and in other embodiments of 0.9:1 to 1.2:1 or 0.9:1 to 1.1:1). For the octasalt the Al/Zr atomic ratio is 6.2:1 to 10.0:1 and the Betaine:Zr mole ratio is 0.2:1 to 3.0:1 (or in other embodiments of 0.4:1 to 1.5:1). In one embodiment, in the case of a salt that contains zirconium, the Betaine is incorporated during the synthesis of the salt so as to maximize the stabilizing effect this ingredient has (especially on the zirconium species). Alternatively, it can be post added to a glycine-free salt along with additional active phase ingredients to form a Betaine stabilized active.

Examples of commercially available glycine-free low M:Cl ratio tetrasalts and octasalts include, but are not limited to, REZAL™ AZP 955 CPG and REZAL™ AZP 885 respectively (both from Reheis Chemical Company, Berkeley Heights, N.J.). A more detailed description of making such commercially available salts can be found for example, in U.S. Pat. Nos. 7,074,394 and 6,960,338. Further examples of making these types of salt complexes are described in U.S. Patent Application Publication No. 2004/0198998 and U.S. Pat. No. 7,105,691.

In addition to the anti-irritation properties of Betaine, it has also been found that antiperspirant formulations preserve their fragrance stability upon ageing when the Al/Zr salt is used in association with Betaine.

Additionally, the antiperspirant active can be a calcium salt stabilized antiperspirant active. Examples of calcium salt stabilized antiperspirant actives can be found in U.S. Patent Application Publication No. 2006/0204463, which is incorporated herein by reference only for the disclosure of the calcium salt stabilized antiperspirant actives.

In addition, aluminum nitratohydrate and its combination with zirconyl hydroxychlorides and nitrates, or aluminum-stannous chlorohydrates, can be incorporated as an antiperspirant active. Antiperspirant actives can include, but are not limited to, the following: astringent salt of aluminum, astringent salt of zirconium, aluminum bromohydrate, aluminum chlorohydrate, aluminum dichlorohydrate, aluminum sesquichlorohydrate, aluminum chlorohydrex PG, aluminum dichlorohydrex PG, aluminum sesquichlorohydrex PG, aluminum chlorohydrex PEG, aluminum dichlorohydrex PEG, aluminum sesquichlorohydrex PEG, aluminum chloride, aluminum sulfate, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorhydrex propylene glycol, aluminum zirconium trichlorohydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate. In one embodiment, the antiperspirant active is aluminum chlorhydrate. In another embodiment, the antiperspirant active is aluminum zirconium tetrachlorhydrex propylene glycol.

Deodorant Active Materials

Any known deodorant active can be used. Examples of deodorant active include, but are not limited to, antimicrobial actives, alcohols, 2,4,4'-trichloro-2'-hydroxy diphenyl ether (Triclosan), benzethonium chloride, polyhexamethylene biguanides, triethylcitrate, 2-amino-2-methyl-1-propanol (AMP), cetyl-trimethylammomium bromide, cetyl pyridinium chloride, farnesol (3,7,11-trimethyl-2,6,10-dodecatrien-1-ol), bactericides, and/or bacteriostats.

Emollients

The composition can contain emollients in any desired amount to achieve a desired emollient effect. Emollients are known in the art and are used to impart a soothing effect on the skin. Non-volatile emollients are preferable in the present invention. Classes of non-volatile emollients include non-silicone and silicone emollients. Non-volatile, non-silicone emollients include $C_{12-15}$ alkyl benzoate. The non-volatile silicone material can be a polyethersiloxane, polyalkyarylsiloxane or polyethersiloxane copolymer. An illustrative non-volatile silicone material in the present invention is phenyl trimethicone. Non-limiting examples of emollients can be found in U.S. Pat. No. 6,007,799. Examples include, but are not limited to, PPG-14 butyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate), Di-(2-ethyl hexyl)succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide.

The composition can additionally include ionizable inorganic salts. These ionizable salts are of the form $M_aX_b$ where a=1, or 2 and b=1 or 2; M is a member chosen from $Na^{+1}$, $Li^{+1}$, $K^{+1}$, $Mg^{+2}$, $Ca^{+2}$, $Sr^{+2}$, and $Zn^{+2}$ and X is a member chosen chloride, bromide, iodide, citrate, gluconate, lactate, glycinate, glutamate, ascorbate, aspartate, nitrate, phosphate, hydrogenphosphate, dihydrogenphosphate, formate, maloneate, maleate, succinate, carbonate, bicarbonate, sulfate, and hydrogensulfate. In certain embodiments, the selected salts are chosen from NaCl and $ZnCl_2$. As will be appreciated by those skilled in the art, while it may be possible under certain circumstances to add a salt directly to a portion of the mixture during manufacturing, it is desired to add the salt as a mixture or solution of the salt in a carrier or solvent, particularly water. Of course various concentrations of the salt premix can be made.

The composition may also contain particulates which include but are not limited to talc, mica, fragrance encapsulates, or hydrophobically modified starches, such as aluminum starch octenyl succinate (MACKADERM™ ASTRO-DRY™ from McIntyre Group Ltd.). If the composition is in a liquid form and dispensed through a roll-on applicator, the average particle size of the suspended material is sized so that it can pass through the application to prevent the ball applicator from malfunctioning. Usually, the average particle size does not exceed 150 microns.

In certain embodiments, the composition may also contain as an optional ingredient at least one malodor counteracting alpha, beta-unsaturated ester or mixtures of such materials. In certain embodiments, the level of malodor counteracting composition to deliver a perceivable odor control benefit when delivered from an antiperspirant and/or deodorant composition is 0.05 to 0.45 weight % based on the entire composition. The alpha, beta-unsaturated ester malodor counteracting materials are incorporated within the oil phase of an antiperspirant composition. Example of these malodor counteracting components can be found in U.S. Pat. Nos. 6,610, 648 and 6,495,097, which are incorporated herein only for their disclosure of the alpha, beta unsaturated esters. For example, in this invention the odor neutralizing alpha, beta unsaturated ester mixture demonstrates unexpected stability in antiperspirant compositions containing low metal:chloride (M:Cl) ratio salts free of glycine. Examples of the alpha, beta unsaturated ester can be found in WO2005/025523, which was filed in the U.S. as U.S. application Ser. No. 10/571,488, both of which are incorporated herein by reference to the extent that they do not conflict with the disclosure in this specification.

Examples of the alpha, beta unsaturated ester include, but are not limited to:

(1) 3-phenyl-2-propenoic acid alkyl esters wherein $R^1$ is a substituent on the benzene ring and is chosen from an alkyl, an alkoxy, an aryl, or a substituted aryl. In certain embodiments, $R^1$ is chosen from H, a $C_1$ to $C_8$ alkyl, a $C_1$ to $C_8$ alkoxy, or an aryl; and $R^2$ is a subsistent group replacing the carboxylic acid hydrogen to form the ester where $R^2$ has greater than 6 carbon atoms, an aryl, or a substituted aryl group, in certain embodiments $R^2$ is a $C_6$ to $C_{12}$ alkyl or is a benzyl group; and (2) an ester of fumaric or maleic acid having linear ester carbon chains from 3-9 carbons, for example dihexyl fumarate;

(3) e-phenyl propenoic acid ester chosen from octyl methoxy cinnamate, phenylethyl cinnamate, benzyl cinnamate;

(4) an aliphatic unsaturated ester, such as dihexyl fumarate.

The composition may optionally further comprise absorbent materials such as corn starch, talc, clay, sodium polyacrylate and/or cotton fiber; and/or other materials such as fragrances, bacteriostats and/or bacteriosides, colorants, etc. Known bacteriostats include baceteriostatic quaternary ammonium compounds such as 2-amino-2-methyl-1-propanol (AMP), cetyl-trimethylammomium bromide, cetyl pyridinium chloride, 2,4,4N-trichloro-2N-hydroxydiphenylether (Triclosan), etc. and various zinc salts.

Antioxidants may be added to the composition, preferably to act as ingredient protectants and for maintenance of long-term stability of the composition. Suitable antioxidants include Tinogard, manufactured by Ciba Specialty Chemicals, Basel, Switzerland.

The compositions as provided herein are described and claimed with reference to their ingredients, as is usual in the art. As would be evident to one skilled in the art, ingredients may in some instances react with one another, so that the true composition of the final formulation may not correspond exactly to the ingredients listed. Thus, it should be understood that the invention extends to the product of the combination of the listed ingredients.

The individual component compositions of the present invention may be manufactured using method steps generally known in the art. Typically, the ingredients are combined and heated to melt the components (other than inert filler), and the melted components (together with particulate inert filler) are mixed. Desirably, volatile materials, such as the fragrance materials, are incorporated in the composition in the latter stages of the mixing cycle, in order to avoid volatilization thereof. After mixing, the molten composition can be poured directly into the dispensers, as discussed herein in detail concerning the sequential pouring of the two components, after which the compositions harden into a solid, and the container is capped to preserve the product until use.

Method for Filling the Personal Care Composition into a Container

This invention also relates to a method for filling into a container a multi-component topical personal care composition in a diffuse pattern where the components have at least one visually discernable different characteristic, such as a marbleized appearance. This produces a solid body of the topical personal care composition which has an aesthetic appearance to the purchaser and/or user of the product. More particularly, the container, or a portion thereof such as a removable cap, may be transparent or translucent, such that the aesthetic topical personal care composition presents a unique appearance at the exterior of the container prior to use, or if the container is opaque, such that the aesthetic topical personal care composition presents a unique appearance at the exposed portion of the composition for application to the skin during use.

The present process will produce containers filled with two or more components in a diffuse pattern design. The precise patterns and the intensity of the patterns are the result of the process parameters in the filling of the containers, and the properties of the components of the topical personal care composition. The process parameters include, inter alia, the temperatures, and associated melting temperature, of the first and the second components which are filled, as molten liquids, into the container, the amount of each of the first component and of the second component the shape of the container, and motion of the container during the filling process, for example the degree and rate of oscillation of the container.

Figure 2:
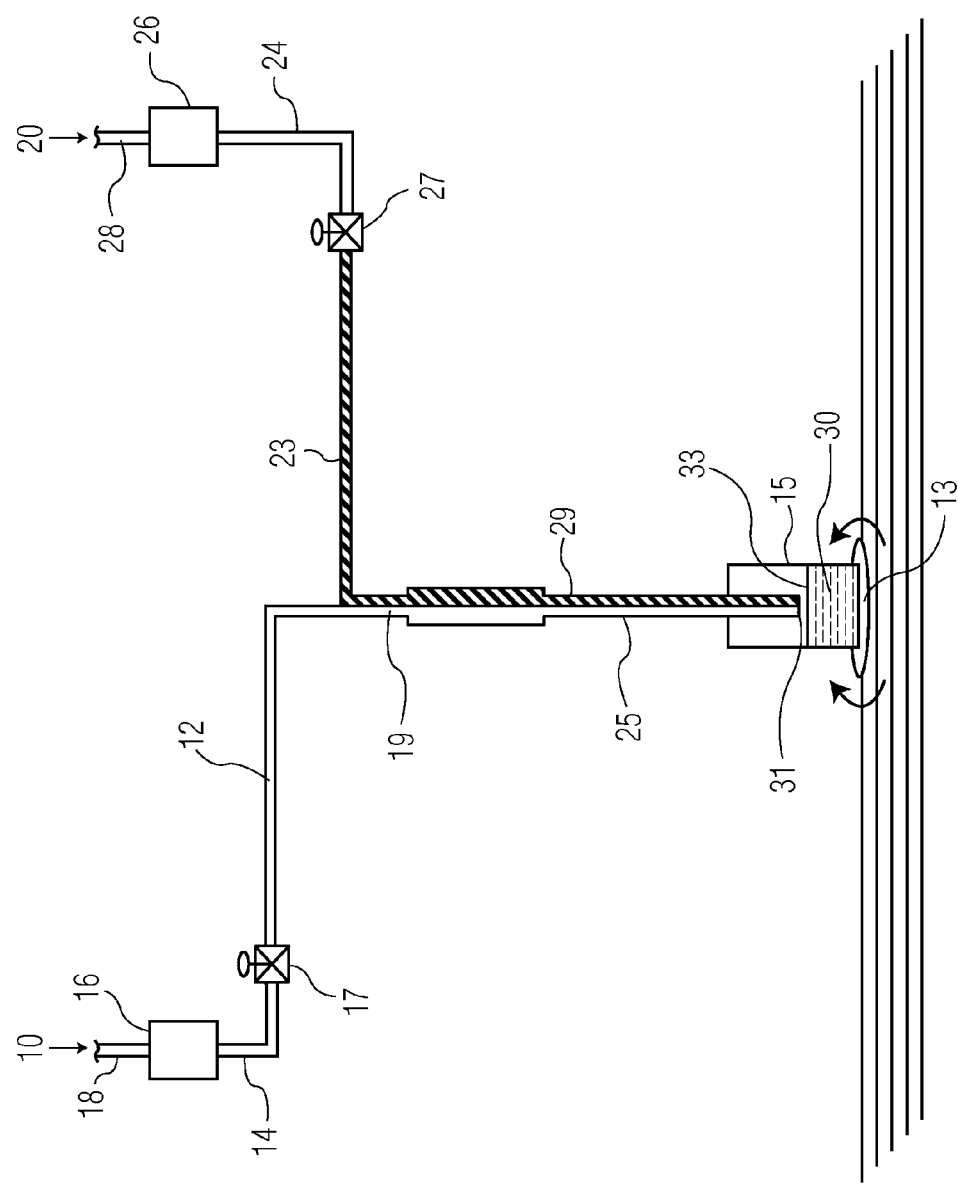
FIG. 2 is a schematic elevation view of a layout diagram of a process of filling a container according to a method of another embodiment of the present invention.

FIG. 2 is a layout diagram of one embodiment of the filling apparatus. In FIG. 2 a container 15 is at an early stage of being filled with the first component 30 in molten form. There are two separate components needed to produce the product in the container 15. These are a first component 10 and a second component 20. The first component 10 and the second component 20 are visually distinct from each other.

The first component 10 is fed into a heated reservoir 16 through an input conduit 18. Heated reservoir 16 maintains the first component at a respective preset temperature in molten form. The first component exits the heated reservoir 16 through an exit conduit 14 to a valve 17. The first component 10 flows from the valve 17 though feed conduit 12 and then through a first component output conduit 19 of a nozzle 25 having an outlet 31. The valve 17 controls the time of injecting for the first component 10 and a flow meter (not shown) may measure the required volume corresponding to the desired mass of that component to be injected into the container 15.

The second component 20 is correspondingly fed into a heated reservoir 26 through an input conduit 28. Heated reservoir 26 maintains the second component at a respective preset temperature in molten form. The second component exits the heated reservoir 26 through an exit conduit 24 to a valve 27. The second component 20 flows from the valve 27 though feed conduit 23 and then through a second component output conduit 29 of the common nozzle 25. The valve 27 controls the time of injecting for the second component 20 and a flow meter (not shown) may measure the required volume corresponding to the desired mass of that component to be injected into the container 15.

All of the conduits are thermally insulated as required to ensure that the components 10, 20 are injected onto the container 15 in a molten state at the required temperatures.

Initially, the required measured volume of the first component 10 is injected to partly fill the container 15. Subsequently, the required measured volume of the second component 20 is injected into the container 15 to completely fill the container 15. The first component 10 is at a lower temperature than the second component 20. As the composition cools, for example by application of forced cooling, such as by passage through a cooling tunnel, the second component 20 solidifies within the molten first component 10.

During injection of at least the second component 20 and preferably also during injection too of the first component 10, the container 15 is supported on a rotatable support 13 that is rotated throughout the filling process, and optionally for a short period hereafter. While any degree of rotation can be used, the rotation is typically in a first direction through at least 90 degrees, and then in a second direction through at least 90 degrees. In order to achieve the desired marbleized random pattern, preferably the container 15 is first rotated in a first direction and then in a second direction in an oscillating motion. The oscillations of a rotation in a first direction and then in a second direction may be related to the flow rate of the first component 10 and second component 20 into the container 15 to fill the container 15. The container is typically rotated at least 90 degrees in the first direction and at least 90 degrees in the second direction, preferably at least about 180 degrees in the first direction and at least about 180 degrees in the second direction.

The nozzle may extend within the container at the initiation of the filling of the container and be separated from the container during the filling of the container by relative withdrawal of the nozzle from the container or the container being withdrawn from the nozzle.

During this process, the nozzle 25 is maintained above fill level 33 of the product 30 in the container 15. This may be accomplished by either raising the nozzle 25 upward or by lowering the container support 13. It is preferred to raise the nozzle 25. The oscillations may be through about 120 degrees to about 480 degrees and may comprise about 1 oscillation to about 10 oscillations and preferably about 2 to 7 oscillations to fill a container 15.

Figure 3:
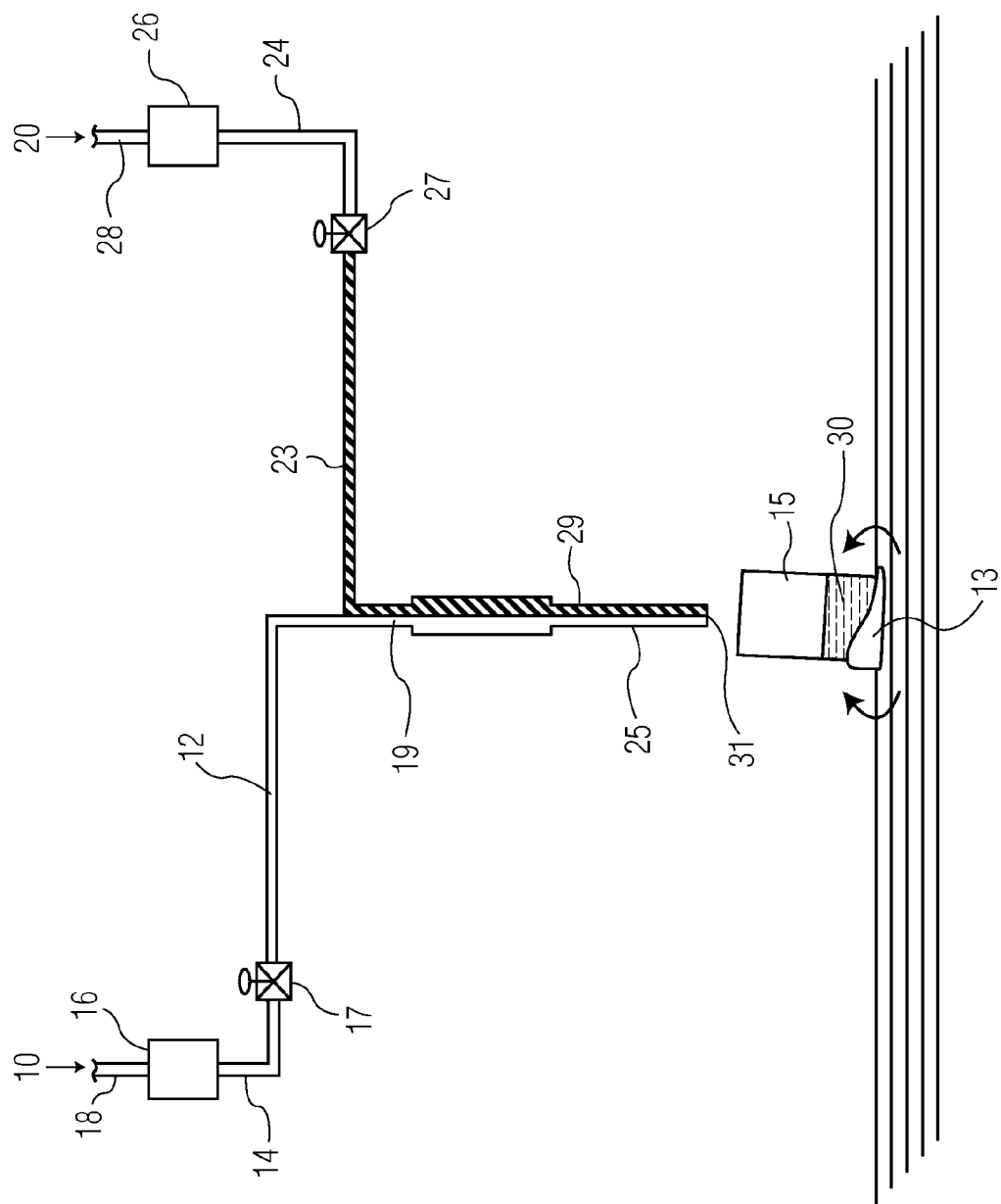
FIG. 3 is a schematic elevation view of a layout diagram of a process of filling a container according to a method of a further embodiment of the present invention in which the support for the container is tilted at an angle to the filling nozzle.

FIG. 3 is a further embodiment of the filling apparatus of FIG. 2 but with the rotatable container support 13 tilted at an angle to the horizontal so that the container axis is inclined to the nozzle 25 and to the vertical by an angle of typically up to about 20 degrees. Thus the container 15 is tilted at an angle to the nozzle 25 as it is being rotated and filled. The angling may be at an angle of about 3 degrees to about 20 degrees, typically up to about 15 degrees, to the nozzle 25.

In another embodiment, not illustrated, the support 13 includes a device to vibrate the support 13 and thereby vibrate the container 15. The vibration may occur while the container 15 is being rotated. The result is that the container 15 is being vibrated while the container 15 is being oscillated and filled with the first component and the second component to produce the random pattern composition 30. The vibration and oscillation do not have to occur at the same time. Additionally, it is not required that the container 15 be oscillated in this embodiment of the invention.

The vibration of the support 13 and the container 15 during the filling of the container will cause the pattern of the product 30 in the container 15 to become more diffuse and will promote product 30 as it exits nozzle 25 to flow away from nozzle 25 to parts of the container that are more distant from the nozzle 25. This will be useful in filling non-circular containers such as oval containers that have an elliptical cross-section. It also will be useful in the filling of non-axial containers. These are containers that are not symmetrical around the axis of the container formed through the container fill and dispensing opening. Both the amplitude and the frequency of the vibrations will depend on the particular formulations.

The color of the first component 10 and the second component 20 may vary. However, the objective usually will be to use contrasting colors so as to make the diffuse design more vibrant and visible. A useful pairing of two components is to have one white and the other a color. With color matching the variations are essentially unlimited. Further, there can be more than two components sequentially injected into the container. There can be three or more components, and in addition, particles or capsules may be included. This will provide a wider range of diffuse patterns to products.

The container 15 may be of essentially any shape, size or material construction. Since the stick products, such as antiperspirant/deodorant stick products, will primarily be consumer product-sized, the containers will contain 25 ml to 2 liters, typically 50 to 100 ml, of product and may be constructed of polyethylene, clarified polypropylene, polyethylene terephthalate and polyvinyl chloride.

EXAMPLE

In the following is set forth an example of the present invention. The example is illustrative, and not limiting, of the present invention. In the following example, all amounts are in percent of the total weight of the composition.

First and second antiperspirant components having the compositions in Table 1 are made using known formulation techniques. Component 1 uses stearyl alcohol as the fatty alcohol co-gellant with hydrogenated soybean oil to produce a relatively low melting point component having a melting point of 47-53° C. Component 2 uses polyethylene as the hydrocarbon co-gellant to produce a alcohol co-gellant with hydrogenated soybean oil to produce a relatively high melting point component having a melting point of 70-76° C. The iodine value of the hydrogenated soybean oil used in the examples is greater than 0 to 1. The weight average molecular weight of the polyethylene used in the examples is indicated by the product number.

TABLE 1

| Stick Composition | Component 1 | Component 2 |
|---|---|---|
| Cyclomethicone (DC245 from Dow Corning) | 15.2 | 13.6 |
| C$_{12-15}$ alkyl benzoate | 6 | 17.1 |
| Stearyl alcohol | 15.8 | 0 |
| Polyethylene | 0 | 11 |
| PEG-8 distearate | 3.4 | 4.3 |
| Hydrogenated soybean oil | 3.4 | 4.3 |
| Antiperspirant Active Z576 | | 22.4 |
| Antiperspirant Active 908 | 20.4 | 0 |
| PPG-14 butyl ether | 6 | 0 |
| Talc | 0 | 0 |
| Behenyl alcohol | 0.2 | 0 |
| Blue Cosmetic Wax (or FD&C Green) | 0 | 0.2 |

Component 1 is heated to a temperature of 66° C., which is above the melting point of Component 1. Component 2 is heated to a temperature of 82° C., which is above the melting point of Component 2. Both components are stored in respective temperature controlled heated reservoirs having a rotary hydrofoil blade rotating at 60-70 rpm. An inverted barrel of a conventional stick container is positioned on a rotatable support plate that is oscillatingly rotated. A measured amount, corresponding to 85 wt % of the final stick product, of the molten Component 1 is injected downwardly into the inverted barrel. Then, after completion of the injection of Component 1, a measured amount, corresponding to 15 wt % of the final stick product, of the molten Component 2 is injected into the molten mass of Component 1. A base is applied to the barrel, and then the barrel is transferred to a cooling tunnel, set at 17-18° C., and allowed to cool for 15-20 minutes prior to conditioning at ambient temperature, and final product labeling.

As the composition cools, Component 2 starts to solidify within the still molten Component 1 and completes solidification before solidification of the lower melting point Component 1. The result is a marbleized appearance throughout the composition. The applied forced cooling of the composition assists minimization of migration or bleeding of the higher melting temperature colored phase into the lower melting temperature white background phase.

Various other modifications to the disclosed embodiments will be apparent to those skilled in the art. In particular, alternative embodiments having a cap fitted to a container so that the package may be selectively stood upright either on its container end or on its cap end may comprise stick dispensers, for dispensing a solid stick of a personal care composition such as an antiperspirant composition and/or a deodorant composition, rather than roll-ball dispensers.

The invention claimed is:

1. A method of forming in a container a random diffuse pattern mixture of at least two components of a solid body of a topical personal care composition, the at least two components having differing visual characteristics, the method comprising the steps of:
   (a) providing a container on a container support capable of moving the container;
   (b) feeding a first component of the at least two components into the container, the first component being molten and at a first temperature above a melting temperature of the first component;
   (c) at least after commencement of step (b), feeding a second component of the at least two components into the molten mass of the first component in the container, the second component being molten and at a second temperature above a melting temperature of the second component, the second temperature being higher than the first temperature and the melting temperature of the first component is at least 23° C. lower than the melting temperature of the second component;

(d) concurrently moving the container on the container support during at least a part of feeding step (c) or after the termination of both feeding step (b) and feeding step (c) to form a random diffuse pattern mixture of the first and second components; and (e) cooling the first and second components to form a solid body having the random diffuse pattern mixture, the second component commencing solidification thereof during the cooling step prior to solidification of the first component.

2. The method according to claim 1, wherein the melting temperature of the first component is 23 to 28° C. lower than the melting temperature of the second component.

3. The method according to claim 1, wherein the first temperature is 57 to 71° C.

4. The method according to claim 3, wherein the first temperature is 62 to 69° C.

5. The method according to claim 1, wherein the second component terminates solidification thereof during the cooling step prior to solidification of the first component.

6. The method according to claim 1, wherein the personal care composition is an antiperspirant composition and/or a deodorant composition.

7. The method of claim 6, wherein the personal care composition is a solid stick or soft solid.

8. The method according to claim 1, wherein the at least two components have different colors.

9. The method according to claim 1, wherein the feeding of the second component in step (c) is commenced after termination of the feeding of the first component in step (b).

10. The method according to claim 1, wherein the container is moved on the container support after the termination of both feeding step (b) and feeding step (c).

11. The method according to claim 1, wherein the container is moved on the container support additionally during at least a part of cooling step (e).

12. The method according to claim 1, wherein the support is rotatable and in step (d) the container is rotated on the container support in at least a first rotational direction.

13. The method according to claim 12, wherein the container is rotated on the container support in an oscillating manner in the first rotational direction and in an opposite second rotational direction.

14. A method according to claim 12, wherein the container is rotated at least 90 degrees in a first direction and at least 90 degrees in a second direction.

15. A method according to claim 14, wherein the container is rotated up to about 360 degrees in a first direction and up to about 360 degrees in a second direction.

16. A method according to claim 14, wherein the container is rotated up to about 270 degrees in the first direction and up to about 270 degrees in the second direction.

17. A method according to claim 1, wherein the container support maintains the container vertically tilted at an angle of up to about 20 degrees.

18. A method according to claim 1, wherein the container is subject to a vibration during the feeding of at least the second component to the container.

19. A method according to claim 1, wherein the first and second components are fed into the container from a nozzle having two inputs and two outputs, one input and output pair for each respective component.

20. The method according to claim 1, wherein the second temperature is 76 to 85° C.

21. The method according to claim 1, wherein the second temperature is 79 to 86° C.

* * * * *